United States Patent [19]
Estanove et al.

[11] Patent Number: 6,124,358
[45] Date of Patent: Sep. 26, 2000

[54] PHARMACEUTICAL COMPOSITION CONTAINING RHEIN OR DIACERHEIN WITH IMPROVED BIOAVAILABILITY

[75] Inventors: Cyril Estanove, Boulogne; Alain Prudhomme, La Foret Fouesnant, both of France

[73] Assignee: Mazal Pharmaceutique (SARL), Quimper, France

[21] Appl. No.: 09/125,514

[22] PCT Filed: Dec. 23, 1997

[86] PCT No.: PCT/FR97/02403

§ 371 Date: Aug. 20, 1998

§ 102(e) Date: Aug. 20, 1998

[87] PCT Pub. No.: WO98/27965

PCT Pub. Date: Jul. 2, 1998

[30] Foreign Application Priority Data

Dec. 23, 1996 [FR] France ................................ 96 15867

[51] Int. Cl.[7] .......................... A61K 31/19; A61K 31/22
[52] U.S. Cl. ......................... 514/548; 514/544; 514/569
[58] Field of Search ................................ 514/544, 548, 514/509

[56] References Cited

U.S. PATENT DOCUMENTS

| | | | |
|---|---|---|---|
| 4,244,968 | 1/1981 | Friedmann | 424/308 |
| 4,344,934 | 8/1982 | Martin et al. | 424/80 |
| 4,895,726 | 1/1990 | Curtet et al. | 424/456 |
| 5,393,898 | 2/1995 | Careasona et al. | 552/262 |
| 5,652,265 | 7/1997 | Vittori et al. | 514/548 |
| 5,856,358 | 1/1999 | Bennetti et al. | 514/563 |

FOREIGN PATENT DOCUMENTS

| | | |
|---|---|---|
| 330532 | 8/1989 | European Pat. Off. . |
| 371431 | 6/1990 | European Pat. Off. . |
| 446753 | 9/1991 | European Pat. Off. . |
| 94/14421 | 7/1994 | WIPO . |

OTHER PUBLICATIONS

Journal of Pharmaceutical Sciences, vol. 84, No. 12, Dec. 1995, pp. 1434–1437, "Effect of Cogrinding with Various Kinds of Surfactants on the Dissolution Behavior of Phenytoin".

Journal of Pharmaceutical Sciences, vol. 65, No. 10, Oct. 1976, pp. 1484–1488, "Dissolution Behavior and Bioavailability of Pheytoin froma Ground Mixture with Microcrystalline Cellulose".

*Primary Examiner*—James H. Reamer
*Attorney, Agent, or Firm*—Burns, Doane, Swecker & Mathis, LLP

[57] ABSTRACT

Provided is a pharmaceutical composition based on rhein or diacerhein. The composition is intended for administration by the oral, rectal or cutaneous (percutaneous or transdermal) route, and comprises rhein or diacerhein, or one of their pharmaceutically acceptable salts or esters, and sodium lauryl sulfate, comicronized, in a weight ratio between 3:1 and 30:1. The composition exhibits improved bioavailability.

9 Claims, No Drawings

PHARMACEUTICAL COMPOSITION CONTAINING RHEIN OR DIACERHEIN WITH IMPROVED BIOAVAILABILITY

FIELD OF THE INVENTION

The present invention relates to a new stable pharmaceutical composition which can be used in human and veterinary therapy, and more particularly a new galenic form adapted to rhein and to diacetylrhein (diacerhein), substantially improving the bioavailability of the active ingredient.

BACKGROUND OF THE INVENTION

Rhein, or 9,10-dihydro-4,5-dihydroxy-9,10-dioxo-2-anthracenecarboxylic acid, and diacerhein, its diacetylated derivative, that is to say 4,5-bis(acetyloxy)-9,10-dihydro-4,5-dihydroxy-9,10-dioxo-2-anthracenecarboxylic acid, are described in numerous scientific publications as well as in patent FR-A-2,508,798. Diacerhein is well known as a medicament having antiarthritic activity, and is used in particular in the treatment of osteoarthritis. However, rhein and diacerhein have the disadvantage of being practically insoluble in water and in alcohols. Furthermore, diacerhein may be administered by the oral route, but it is not completely absorbed by the digestive tract, and this incomplete absorption could cause undesirable side effects, for example laxative effects. Moreover, the administration of rhein is thought to cause even more problems than that of diacerhein.

To overcome these difficulties, various derivatives as well as pharmaceutical compositions and specific galenic forms have been proposed in the literature. For example, patent EP-A-243,968 describes a water-soluble potassium salt of diacerhein which can be used in the preparation of compositions for parenteral administration.

It is known, moreover, that the solubilization and/or wettability of a substance can be improved by treatment by means of a surfactant, which generally has the effect of promoting bioavailability of the active ingredient. It is also known that the grinding of insoluble active ingredients in the presence of certain water-soluble polymers improves the solubility and bioavailability of the product (Yamamoto et al., *J. Pharm. Sci.* (1976) 65, p. 1484–88).

The grinding of the substances used in therapy can be carried out in ball or hammer mills of the customary type. The procedure can also be carried out by micronization in gaseous jet micronizers which have the advantage of not heating the substances to be micronized. The micronization technique has been used to develop a pharmaceutical composition based on bioavailable and orally administerable progesterone whose bioavailability is double that of the crystalline form previously known.

Patent EP-A-330,532 describes the comicronization of fenofibrate in the presence of sodium lauryl sulfate. On the other hand, M. Otsuda et al. (*J.P.S.* 84 (1995) p. 1434–37) have studied the micronization of phenitoin in the presence of a surfactant, and they have shown that the solubility of phenitoin is not improved in the case of comicronization with a surfactant such as sodium lauryl sulfate or a sucrose ester of stearic acid, whereas it is multiplied by 30 compared with the mixture of the powders, in the case of a cogrinding with sodium deoxycholate.

Moreover, even if the micronization or the grinding of a substance in the presence of a surfactant or of a sugar can increase its solubility, these parameters are not always adequate. For example, the bioavailability of micronized progesterone is not adequate and should be improved, for example by dispersion in carnauba wax. Such a technique is described in application WO-89,02742.

Thus, it appears that the properties of a substance treated by micronization or grinding, in particular its solubility and its bioavailability, are not predictable, it being possible to obtain contradictory results. Furthermore, an identical galenic formulation can provide good results with a substance and give the opposite result with another substance.

SUMMARY OF THE INVENTION

The subject of the present invention is a new stable pharmaceutical composition based on diacerhein for administration by the oral, rectal or cutaneous (percutaneous or transdermal) route, having improved bioavailability, and more particularly intended for the treatment of inflammatory diseases.

The pharmaceutical composition according to the present invention is distinguished in that it comprises rhein or diacerhein, or one of their pharmaceutically acceptable salts or esters, and sodium lauryl sulfate, comicronized, in a weight ratio of between 3:1 and 30:1.

The pharmaceutical dosage form which can be used in the present invention is suitable for any route of administration involving passage across an epithelium, that is to say more particularly the oral, rectal or cutaneous (percutaneous or transdermal) forms.

The pharmaceutically acceptable salt or ester of rhein may be chosen from the sodium or potassium rheinate esters. Diacerhein itself may be considered as being a specific case, that is to say a salt of rhein (diacetate) and an acid. In the text which follows, the name "rhein" denotes both the acids themselves, that is to say rhein and diacerhein, and the salts or esters.

According to a preferred embodiment of the invention, the weight ratio of rhein to sodium lauryl sulfate is between 6:1 and 15:1.

The subject of the invention is also a process for the preparation of a pharmaceutical composition based on rhein capable of being administered by the oral, rectal or cutaneous (percutaneous or transdermal) route, and having an improved bioavailability, consisting in comicronizing rhein and sodium lauryl sulfate in a weight ratio of between 3:1 and 30:1, and preferably between 6:1 and 15:1.

DETAILED DESCRIPTION OF THE PREFERRED EMBODIMENTS

The micronization is preferably carried out in a gaseous jet micronizer, and more particularly an air jet or a nitrogen jet micronizer, so as to obtain a powder whose mean particle size is less than 50 $\mu$m, and preferably less than 20 $\mu$m, with a homogeneous particle size distribution.

The mixture of comicronized powders as indicated above can be made in the pharmaceutical dosage form of a capsule, a hard gelatin capsule, a cream, an ointment, a suppository or a tablet, containing, in addition, customary excipients. In the case of forms which can be administered by the oral route, there may be used, for example, diluents such as lactose, cellulose and sugars, lubricants such as magnesium stearate and stearic acid, disintegrating agents such as starch glycolate and carboxy-methylcellulose, anticaking agents such as silica, binding agents such as polyvidone, film-forming compounds such as hydroxypropylmethylcellulose and acrylic lacquers, plasticizers such as dibutyl sebacate and polyethylene glycol, sweeteners such as aspartame and sodium saccharinate, opacifiers such as talc and titanium dioxide, colorants such as iron oxides, flavorings, preservatives such as methyl parahydroxybenzoate. In the case of the cutaneous or percutaneous forms, there may be used excipients with fatty and aqueous phases (petroleum jelly and water), surfactants and emulsifiers such as sorbitan esters and glycerol monostearate, thickeners such as ketostearyl alcohol, gelling agents such as carbomers and sodium carboxymethylcellulose and preservatives such as parahydroxybenzoates. In the specific case of the transdermal form, there may be used plasticizers such as triacetin and polymers such as methacrylates. The form which can be administered by the rectal route may comprise lipophilic and hydrophilic excipients such as glycerides, polyoxyethylene glycols and suppocires®. The total quantity of excipients in the composition generally varies according to the pharmaceutical dosage form used, and may represent between about 50 and 99% of the total weight of the composition.

The improvements made to the bioavailability of rhein by the composition of the invention, compared with the conventional pharmaceutical dosage forms, make it possible to reduce the content of active ingredient in the medicament. Thus, in the case of a formulation as a hard gelatin capsule for oral administration, or of a formulation for administration by the rectal route, the composition according to the invention generally contains between 20 mg and 50 mg of active ingredient per unit dose.

Finally, the subject of the invention is the use of comicronized rhein and sodium lauryl sulfate for the preparation of a medicament for the treatment of inflammatory diseases, and in particular of osteoarthritis.

It was observed, during tests carried out with the composition of the invention, that the comicronization of sodium lauryl sulfate with rhein causes no degradation of the latter, even in the case of diacerhein, that is to say in the form of an ester, which is a product sensitive to bases, whereas tests of micronization with another surfactant such as sodium deoxycholate show degradation of the active ingredient which is higher, the higher the surfactant concentration.

Moreover, measurements of the speed of dissolution with several surfactants (surfactant/active ingredient weight ratio=1:4; grinding with a pestle; grinding time 4 minutes) gave the results indicated in the following table (T being the time, expressed in minutes, necessary to dissolve 100% of the active ingredient):

| Surfactant | T |
| --- | --- |
| Sodium lauryl sulfate | 2 |
| Sucrose ester HLB15* | 12 |
| Sodium deoxycholate | 20 |

*HLB = hydrophilic-lipophilic balance, system of classification of surfactants developed by Griffin. The HLB value varies from 0.5 to 20, corresponding to lipophilic and hydrophilic characters, respectively.

These results, in particular the improvement of the speed of dissolution with sodium lauryl sulfate, are unexpected taking into account those described by Otsuda et al. (cited above) for the same surfactants comicronized with phenitoin.

The comparative tests of speed of dissolution in vitro, carried out with compositions in accordance with the invention, on the one hand, and compositions containing the non-micronized active ingredient combined with a surfactant, micronized or otherwise, on the other hand, gave the following results:

|  | 20 min. | 30 min. | 90 min. |
| --- | --- | --- | --- |
| Non-micronized diacerhein + non-micronized surfactant | 60% |  | 80% |
| Non-micronized diacerhein + micronized surfactant | 60% |  | 80% |
| Composition of the invention | 95% | 100% | 100% |

It can be seen that the speed of dissolution of the active ingredient is markedly improved in the composition in accordance with the invention Bioequivalence studies in 10 healthy volunteers were carried out according to a double blind design, with a randomization table, between hard gelatin capsules containing 50 mg doses of diacerhein in a commercialized form and hard gelatin capsules containing 50 mg doses of diacerhein and 5.6 mg of sodium lauryl sulfate, comicronized, according to the invention.

The results obtained have made it possible to show that the improvement in absorption linked to the comicronization of diacerhein comicronized with the surfactant is of the order of 30% compared with the original product.

These results were confirmed by a second double blind bioequivalence study in 22 healthy volunteers, for which the original formulation of 50 mg of diacerhein proved to be comparable to a formulation in accordance with the present invention, containing 35 mg of diacerhein and 3.9 mg of sodium lauryl sulfate, comicronized, as regards the pharmacokinetic characteristics represented by the Cmax (plasma concentration), Tmax (time necessary to reach Cmax) and the AUC (area under the curve) values.

Furthermore, the tests carried out have shown that the composition according to the invention has an excellent stability over time.

The examples of formulation below are given with no limitation being implied to illustrate the invention.

EXAMPLE 1

10 kg of diacerhein and 1 kg of solid sodium lauryl sulfate are successively introduced into a cube mixer and mixed until a homogeneous powder is obtained.

The mixture of powders thus obtained is comicronized in a gas jet mill. A powder is thus obtained whose particle size profile, determined by laser particle size grading, is in unimodal Gaussian form, containing particles with a mean size of less than 10 $\mu$m.

The excipients indicated below are added to this mixture in order to obtain the following composition per hard gelatin capsule No. 1:

| diacerhein | 17.5 mg |
| --- | --- |
| sodium lauryl sulfate | 1.75 mg |
| cellulose | 267.5 mg |
| magnesium stearate | 4.5 mg |

EXAMPLE 2

The procedure is carried out as in Example 1, and 10 kg of diacerhein and 0.75 kg of sodium lauryl sulfate are successively introduced into an appropriate cube mixer.

The mixture is comicronized in a gas jet mill, as in Example 1, and a powder is thus obtained whose particle size profile, determined by laser particle size grading, is of the unimodal Gaussian form, containing particles with a mean size of less than 10 μm.

The excipients indicated below are added to this mixture in order to obtain the following composition per hard gelatin capsule No. 1:

| | |
|---|---|
| diacerhein | 40 mg |
| sodium lauryl sulfate | 3 mg |
| lactose | 230 mg |
| starch | 20 mg |
| talc | 2 mg |
| magnesium stearate | 10 mg |

We claim:

1. A pharmaceutical composition based on rhein or diacerhein for administration by the oral, rectal or cutaneous route, comprising rhein or diacerhein, or one of their pharmaceutically acceptable salts or esters, and sodium lauryl sulfate, comicronized, in a weight ratio of between 3:1 and 30:1.

2. The composition according to claim 1, wherein the weight ratio of rhein or of diacerhein to sodium lauryl sulfate is between 6:1 and 15:1.

3. The composition according to claim 1, wherein the mean size of the rhein or diacerhein and sodium lauryl sulfate particles is less than 20 μm.

4. The composition according to claim 1, wherein the composition contains from 20 mg to 50 mg of rhein or of diacerhein per unit dose.

5. A process for the preparation of a pharmaceutical composition based on rhein or on diacerhein with improved bioavailability, by micronization of the active ingredient, the process comprising comicronization of rhein or of diacerhein, or of one of their pharmaceutically acceptable salts or esters, and of sodium lauryl sulfate in a weight ratio of between 3:1 and 30:1.

6. The process according to claim 5, wherein the micronization is carried out in a gaseous jet micronizer.

7. A medicament for the treatment of inflammatory disease comprising the pharmaceutical composition of claim 1.

8. Treatment of an inflammatory disease by administering by oral, rectal or cutaneous route the pharmaceutical composition of claim 1.

9. The treatment of claim 8, wherein the inflammatory disease treated is osteoarthritis.

* * * * *